United States Patent [19]

Yunker et al.

[11] Patent Number: 5,084,276

[45] Date of Patent: Jan. 28, 1992

[54] QUINOLONE CARBOXYLIC ACID COMPOSITIONS WITH POLYMERIC ADDITIVE TO REDUCE VEIN IRRITATION

[75] Inventors: Martin H. Yunker; Jacqueline E. Briskin, both of Waukegan; David L. Schwinke, Vernon Hills, all of Ill.

[73] Assignee: Abbott Laboratories, Abbott Park, Ill.

[21] Appl. No.: 461,159

[22] Filed: Jan. 5, 1990

[51] Int. Cl.$^5$ .............. A61K 9/08; A61K 47/36; A61K 47/40; A61K 31/47
[52] U.S. Cl. .............................. 424/422; 514/773; 514/774; 514/776; 514/778; 514/777; 514/974; 514/254
[58] Field of Search .............. 424/422, 80; 514/59, 514/60, 312, 774, 776, 778, 974; 523/122

[56] References Cited

U.S. PATENT DOCUMENTS

| | | | |
|---|---|---|---|
| 4,141,990 | 2/1979 | Scherrer | 514/470 |
| 4,147,767 | 4/1979 | Yapel, Jr. | 424/489 |
| 4,772,605 | 9/1988 | Naik et al. | 544/101 |
| 4,851,418 | 7/1989 | Sanchez | 514/300 |
| 4,904,659 | 2/1990 | Atwell et al. | 514/234.5 |

Primary Examiner—Thurman K. Page
Assistant Examiner—Edward J. Webman
Attorney, Agent, or Firm—Andreas M. Danckers; Steven R. Crowley

[57] ABSTRACT

Compositions and methods for treating bacterial infections are disclosed. Compositions of a quinolone carboxylic acid or a pharmaceutically acceptable salt or metal ion-acid complex thereof and a polymeric additive that reduces vein irritation upon infusion are described and utilized as antibacterial agents. The compositions of the present invention are parenterally administered to a patient.

5 Claims, No Drawings

QUINOLONE CARBOXYLIC ACID COMPOSITIONS WITH POLYMERIC ADDITIVE TO REDUCE VEIN IRRITATION

TECHNICAL FIELD

The present invention is directed to compositions containing quinolone carboxylic acids or a pharmaceutically acceptable salt or metal ion-acid complex thereof and their use in treating bacterial infections.

BACKGROUND OF THE INVENTION

Quinolone carboxylic acids are known to be effective antibacterial agents. Some of these compounds are known to cause vein irritation upon infusion and accordingly, adversely affect the use of these compounds for parenteral administration to patients.

One especially effective quinolone carboxylic acid antibacterial compound is Temafloxacin. Temafloxacin is a quinolone 3-carboxylic acid represented by the formula:

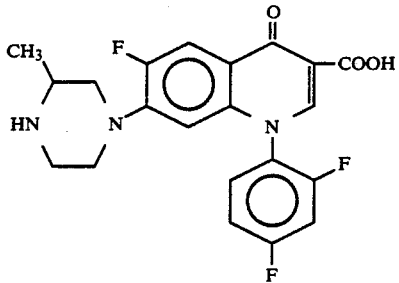

having the chemical name 1-(2,4-difluorophenyl)-6-fluoro-1,4-dihydro-7-(3-methyl-1-piperazinyl) -4-oxo-3-quinoline carboxylic acid, and is disclosed in U.S. Pat. No. 4,730,000 to Chu.

Temafloxacin and its derivatives and salts have antibacterial activity and are useful for combating bacterial infections in warm-blooded animals.

Parenterally administrable compositions of quinolone carboxylic acids have been prepared as reported in European Patent Application No. 0287 926 to Press et.al.; and U.S. Pat. Nos. 4,808,583 and 4,705,789 to Grohe et al.

Solutions of quinolone carboxylic acids that reduce vein irritation and are suitable for parenteral administration to human or veterinary patients have not been reported in the literature.

SUMMARY OF THE INVENTION

The present invention is directed to compositions of a quinolone carboxylic acid or a pharmaceutically acceptable salt or metal ion-acid complex thereof, such as Temafloxacin, that are useful for parenteral administration to a human or veterinary patient.

The compositions of the present invention comprise a quinolone carboxylic acid or a pharmaceutically acceptable salt or metal ion-acid complex thereof, such as temafloxacin, and an additive such as dextran, human serum albumin or polyvinylpyrrolidone, dissolved or dispersed in a physiologically acceptable carrier.

Methods of preparing a composition of a quinolone carboxylic acid or a pharmaceutically acceptable salt or metal ion-acid complex thereof, are also encompassed within the present invention.

The methods of preparing a composition of the present invention comprise dissolving or dispersing the quinolone carboxylic acid or a pharmaceutically acceptable salt or metal ion-acid complex thereof, and the additive in a physiologically acceptable carrier.

Methods of reducing vein irritation upon infusion of quinolone carboxylic acids or a pharmaceutically acceptable salt or metal ion-acid complex thereof, are also encompassed within the present invention.

The methods of treating bacterial infection while reducing vein irritation upon infusion comprise parenterally administering to a human or veterinary patient a composition comprising a quinolone carboxylic acid or a pharmaceutically acceptable salt or metal ionacid complex thereof, such as toxyfloxacin, pefloxacin, temafloxacin, and an additive, such as dextran, human serum albumin or polyvinylpyrrolidone at a therapeutically effective dosage to treat a bacterial infection while reducing vein irritation.

DESCRIPTION OF PREFERRED EMBODIMENTS

The present invention is directed to compositions of a quinolone carboxylic acid or a pharmaceutically acceptable salt or metal ion-acid complex thereof, that are useful for treating bacterial infections and reduce vein irritation.

A composition of the present invention comprises a quinolone carboxylic acid, such as 1-(2,4-difluorophenyl)-6-fluoro-1,4-dihydro-7-(3-methyl-1-piperazinyl)-4-oxo-3-quinolone carboxylic acid (temafloxacin), and an additive, such as dextran, human serum albumin or polyvinylpyrrolidone, dissolved or dispersed in a pharmaceutically acceptable carrier.

Other quinolone carboxylic acids, as for example, Ciprofloxacin, 1-cyclopropyl-6-fluoro-1,4-dihydro-7-(1-piperazinyl)-3-quinolone carboxylic acid, tosufloxacin and the like are also useful in the compositions of the present invention.

As used herein the term "dextran" refers to a polymer of glucose in which the glucosidic linkages are predominately of the (1→6) type.

As used herein the term "human serum albumin" refers to a nonpyrogenic preparation of serum albumin (protein) obtained by fractionating blood, plasma, serum or placentas.

As used herein the term "polyvinylpyrrolidone" refers to a polymer comprising linear 1-vinyl-2-pyrrolidone groups.

As used herein the term "pharmaceutically acceptable salts" refers to the pharmaceutically nontoxic acid addition or alkali or alkaline earth metal salts of the quinolone carboxylic acids. These salts can be prepared in situ during the final isolation and purification of the quinolone carboxylic acid, or by separately reacting the base or acid functions with a suitable organic or inorganic acid or base, respectively. Representative acid addition salts include the hydrochloride, hydrobromide, sulfate, bisulfate, acetate, oxalate, phosphate, tosylate, citrate, maleate, fumarate, succinate, tartrate, napsylate, glucoheptonate, lactobionate, lauryl sulfate salts and the like. Representative alkali metal or alkaline earth metal salts include the sodium, calcium, potassium and magnesium salts and the like.

As used herein, the term "pharmaceutically acceptable metal ion-acid complexes" refers to the complex resulting from association of a quinolone carboxylic acid with a metal ion and an organic or inorganic acid.

In addition, such complexes can have associated with them a basic counterion. Representative metal ions include magnesium, calcium, manganese, zinc, cadmium, ferrous, aluminum, iron (III), cerium (IV) and the like. Representative organic acids include lactic, acetic, nicotinic, lactobionic, isethionic, glucuronic and cysteic acids, and the like. Representative inorganic acids include hydrochloric, phosphoric, sulfuric and nitric acids, and the like. Representative organic bases include lysine, arginine, ethylenediamine, choline, ethanolamine, dibenzylethylenediamine and the like.

Other additives that can be utilized to reduce vein irritation in the compositions of the present invention include other proteins such as gelatin, other polysaccharides such as cyclodextrins and their derivatives, hetastarches and polyethylene glycol.

The additives can be present in the pharmaceutical compositions of the present invention in varying concentrations, but it is presently preferred that the amount be less than 25% by weight of the total composition.

As used herein, the term "physiologically acceptable carrier" refers to a diluent useful for administering the active compound of the present invention that is compatible with the other ingredients of the composition and not deleterious to the patient. The physiologically acceptable carrier can take a variety of forms, depending upon the formulation desired for administration and the intended route of administration. Illustrative carriers include water, physiological saline, Ringer's solution, and the like.

The compositions of the present invention can be prepared by dissolving or dispersing the quinolone carboxylic acid and the additive in a physiologically acceptable carrier by conventional means.

Similarly the compositions of the present invention can be parenterally administered to human and veterinary patients to produce a desired antibacterial effect while reducing vein irritation in the patient upon infusion.

The present invention is further illustrated by the following representative EXAMPLES, that are not intended to be limiting.

EXAMPLE 1

261.0 mg, temafloxacin-HCl is added to approximately 540 ml of water for injection and mixed until dissolved. The pH is adjusted to 4.1±0.1 by addition of 1N sodium hydroxide or 1N hydrochloric acid, as needed. Dextrose (2.73 g) and dextran 40 (15 g) are added with mixing and additional water is added until the total volume is 600 ml. If necessary, the pH is again adjusted to 4.1±0.1 as described above. The solution is then passed through a 0.2 micron filter and stored in a sterile container.

EXAMPLE 2

Magnesium dichloride-hexahydrate (266.8 mg) is added with mixing to water (45 ml). Temafloxacin-HCl (239.2 mg) is added with mixing to form an even suspension and L-arginine (93.5 mg) is added with mixing. Dextrose (1.5015 g) is then added with further mixing and the pH adjusted, if needed, to 6.9±0.1 with 1N HCl or additional L-arginine. Human serum albumin (HSA) (5.5 ml of 25% solution) is added with mixing and additional water is added until the total volume is 55 ml. If necessary, the pH is again adjusted to 6.9±0.1 as described above and the solution is passed through a 0.2 micron filter and stored in a sterile container.

EXAMPLE 3

Temafloxacin (3.2 g) and methanesulfonic acid (7.4 ml of a 10% by weight solution) are added with mixing to approximately 650 ml of water. Dextrose (36.4 g) is added with mixing and polyvinylpyrrolidone (pvp) (average M.W. 17,000) (20 g) is then added with mixing. Additional water is added until the volume is 800 ml and the pH is then adjusted to 4.2±0.1 with 1 N HCl or 1N NaOH. The mixture is then filtered through a 0.2 micron filter and stored in a sterile container.

EXAMPLE 4

A rat tail vein irritation study is performed in which rats were given 100 mg temafloxacin/kg/day via the tail vein for 5 days. The concentration of all dosing solutions was 4 mg/ml; and the rate of infusion was 0.15 ml/min. The rats weighed 170–300 grams at the start of the study. Six rats (3/sex/group) were tested with each formulation. All animals were observed for vein irritation at 1–2 hours and approximately 24 hours after each dosing. The results which demonstrate the effectiveness of representative compositions of the present invention are as follows:

A: Vehicle controls (%5 dextrose in Water)

No vein irritation

B: temafloxacin methanesulfonate (4 mg/ml as Temafloxacin)

Blue or purple discoloration of a portion or the entire length of the tail was observed at 1–2 hours after dosing. The tails were found to have recovered or improved at 24 hours after dosing. Discoloration of the tail was first observed after the first dosing. One animal was not dosed on study days 2 and 4 due to vein irritation.

C: temafloxacin methanesulfonate (4 mg/ml as Temafloxacin) with 2.5% PVP

Two animals showed red discoloration which progressed to blue and covered about half the tail, over the course of treatment. Several other animals showed a "flushed" appearance to the tail with some slight discoloration.

D: temafloxacin methanesulfonate (4 mg/ml as Temafloxacin) with 2.5% dextran 40

Some scabbing and bruising at the injection site was noted in one animal on the second day of treatment. The condition of this rat tended to stay the same over the course of the study. After four days of dosing, 4 of 6 animals showed slight bruising at the site of injection but returned to normal 1–2 hours post dose.

E: temafloxacin methanesulfonate (4 mg/ml as Temafloxacin) with 5.0% dextran 40

Rats appeared normal after the first day of dosing. On the second day of dosing, slight bruising around the injection site was noted. One animal could not be dosed on the second day. No further dosing was done on these animals after the second day.

F: temafloxacin HCl (4 mg/ml as Temafloxacin)

Blue discoloration of the distal ¼ to 1κ of the tail was observed at 1–2 hours after dosing. The tails were found to have recovered or improved at 24 hours after dosing. Discoloration of the tail was first observed after the first dosing. Two animals were not dosed on study day 2 and 4, respectively, due to vein irritation. Recoveries in this group of animals were slightly better than the animals of Group B, above

G: temafloxacin hydrochloride (4 mg/ml as Temafloxacin) with 5.0% PVP

Rats appeared normal after the first and second days of dosing. On the third dosing day, bruising was noted in one animal but the other animals could not be dosed due to lack of visualization of veins. No further dosing was done on these animals.

H: Temafloxacin calcium (4 mg/ml as Temafloxacin)

White discoloration of the tail proximal to the point of injection was observed in this group of animals at 1–2 hours after the first dosing. The discolored areas became reddish and bluish at approximately 24 hours after the first dosing. Blue and red discoloration was observed at 1–2 hours after the remaining 4 dosings. Recoveries or improvements were observed at approximately 24 hours after dosings. No difficulty in dosing was experienced in this group of animals.

I: temafloxacin calcium (4 mg/ml as Temafloxacin) with 2.5% HSA

Two animals showed blue to purple discoloration of tails on the first day of dosing. After 5-days of dosing, all animals appear normal.

The above test results indicate that the additives of the present invention reduce vein irritation upon intravenous administration of Temafloxacin.

The foregoing description and the EXAMPLES are intended as illustrative and are not to be taken as limiting. Still other variations within the spirit and scope of this invention are possible and will readily present themselves to those skilled in the art.

We claim:

1. A method of treating a bacterial infection in a patient while reducing discomfort upon infusion of a medication, comprising parenterally administering a therapeutically effective amount of a quinolone carboxylic acid or pharmaceutically acceptable salt or metal ion-acid complex thereof in a composition comprising up to about 25% by weight of an additive selected from the group consisting of gelatin, cyclodextrins, hetastarches, albumin, polyvinylpyrrolidine, dextran, and mixtures thereof that reduces vein irritation.

2. The method of claim 1 wherein said quinolone carboxylic acid is 1-(2,4-difluorophenyl)-6-fluoro-1,4-dihydro-7-(3-methyl-1-piperazinyl) -4-oxo-3-quinolone carboxylic acid.

3. The composition of claim 1 wherein said additive is dextran.

4. The composition of claim 1 wherein said additive is human serum albumin.

5. The composition of claim 1 wherein said additive is polyvinylpyrrolidone.

* * * * *